United States Patent [19]

Knifton et al.

[11] Patent Number: 5,338,890

[45] Date of Patent: Aug. 16, 1994

[54] ONE STEP SYNTHESIS OF METHYL T-BUTYL ETHER FROM T-BUTANOL USING ALKYLSULFONIC ACID-MODIFIED OXIDE CATALYSTS

[75] Inventors: John F. Knifton, Austin; John R. Sanderson, Leander, both of Tex.

[73] Assignee: Texaco Chemical Company, White Plains, N.Y.

[21] Appl. No.: 92,963

[22] Filed: Jul. 19, 1993

[51] Int. Cl.$^5$ ............................................. C07C 41/09
[52] U.S. Cl. ............................................. 568/698
[58] Field of Search ..................................... 568/698

[56] References Cited

U.S. PATENT DOCUMENTS 3,920,582  11/1975  Rona ................................ 568/698

*Primary Examiner*—Howard T. Mars
*Attorney, Agent, or Firm*—James L. Bailey; Kenneth R. Priem; Cynthia L. Kendrick

[57] ABSTRACT

Disclosed is a method wherein t-butanol is reacted with methanol in one step to provide methyl t-butyl ether at a temperature of about 20° C. to 250° C. and a pressure of about atmospheric to about 1000 psig employing a heterogenous catalyst comprising a Group IV oxide having an alkylsulfonic acid covalently bonded thereto, particularly alkylsulfonic acid covalently bonded to silica gel and having the structure:

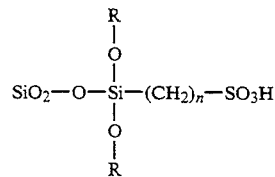

wherein R is an alkyl group having from 1 to 3 carbon atoms and n is an integer in the range of 3 to 10.

9 Claims, No Drawings

ONE STEP SYNTHESIS OF METHYL T-BUTYL ETHER FROM T-BUTANOL USING ALKYLSULFONIC ACID-MODIFIED OXIDE CATALYSTS

CROSS-REFERENCE

This application is related to U.S. Pat. Nos. 4,822,921; 4,827,048; 5,099,072; 5,081,318; 5,059,725; 5,157,162; 5,162,592; 5,157,161; 5,183,947; and allowed U.S. Ser. Nos. 07/917,218; 07/878,121; and 07/917,885, all of which are incorporated by reference.

FIELD OF THE INVENTION

This invention concerns an improved process for preparing methyl tertiary butyl ether (MTBE) by the reaction of tertiary butanol and methanol in the presence of a catalyst comprising an alkylsulfonic acid-modified oxide. MTBE has been generated in up to 40% concentration in the crude product effluent and product phase separation is in evidence at temperatures of 160° C. or greater.

BACKGROUND OF THE INVENTION

It is known to those skilled in the art that ethers, including unsymmetrical ethers, may be prepared by reacting an alcohol with another alcohol to form the desired product. The reaction mixture, containing catalyst and/or condensing agent may be separated and further treated to permit attainment of the desired product. Such further treatment commonly includes one or more distillation operations.

Methyl tert-butyl ether is finding increasing use as a blending component in high octane gasoline as the current gasoline additives based on lead and manganese are phased out. Currently all commercial processes for the manufacture of methyl tert-butyl ether are based upon the liquid-phase reaction of isobutylene and methanol (Eq. 1), catalyzed by a cationic ion-exchange resin with an organic polymer backbone (see, for example: Hydrocarbon Processing, Oct. 1984, p. 63; Oil and Gas J., Jan. 1, 1979, p. 76; Chem. Economics Handbook-SRI, Sept. 1986, p. 543-7051P). The cationic ion-exchange resins used in MTBE synthesis normally have the sulfonic acid functionality and a cross-linked styrene-divinyl-benzene polymer backbone (see: J. Tejero, J. Mol. Catal., 42 (1987) 257; C. Subramamam et al., Can. J. Chem. Eng., 65(1987) 613).

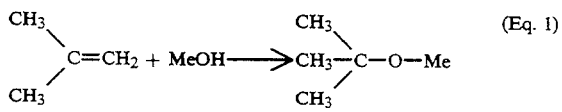

(Eq. 1)

With the expanding use of MTBE as an acceptable gasoline additive, a growing problem is the availability of raw materials. Historically, the critical raw material is isobutylene (Oil and Gas J., Jun. 8, 1987, p. 55). It would be advantageous, therefore, to have a process to make MTBE that does not require isobutylene as a building block. It would be advantageous to have an efficient process for making MTBE by reaction of methanol with tertiary butyl alcohol, since t-butanol (tBA) is readily available commercially through isobutane oxidation.

In U.S. Pat. No. 4,822,921, to Texaco Chemical Co., there is described a method for preparing alkyl tertiary alkyl ethers which comprises reacting a $C_1$-$C_6$ primary alcohol with a $C_4$-$C_{10}$ tertiary alcohol over a catalyst comprising an inert support impregnated with phosphoric acid.

U.S. Pat. No. 4,827,048, to Texaco Chemical Co., describes a method for preparing alkyl tertiary alkyl ethers from the same reactants using a heteropoly acid on an inert support.

U.S. Pat. No. 5,099,072, to Texaco Chemical Co., discloses a method for preparing alkyl tertiary alkyl ethers over an acidic montmorillonite clay catalyst which possesses very specific physical parameters.

U.S. Pat. No. 5,081,318, to Texaco Chemical Co., discloses a method for preparing alkyl tertiary alkyl ethers by reacting a $C_1$-$C_6$ primary alcohol with a $C_4$-$C_{10}$ tertiary alcohol over a catalyst comprising a fluorosulfonic acid-modified zeolite.

U.S. Pat. No. 5,059,725, to Texaco Chemical Co., discloses a method for preparing alkyl tertiary alkyl ethers, including ethyl tertiary butyl ether, from $C_1$-$C_6$ primary alcohols and $C_4$-$C_{10}$ tertiary alcohols over a catalyst comprising ammonium sulfate or sulfuric acid on a Group IV oxide.

U.S. Pat. No. 5,157,162, to Texaco Chemical Co., discloses a fluorosulfonic acid-modified clay catalyst for the production of aliphatic ethers from $C_1$-$C_6$ primary alcohols and $C_4$-$C_{10}$ tertiary alcohols.

In U.S. Pat. No. 5,162,592, to Texaco Chemical Co. there is described a method for producing alkyl tertiary alkyl ethers from $C_1$-$C_6$ primary alcohols and $C_4$-$C_{10}$ tertiary alcohols using a multimetal-modified catalyst.

A hydrogen fluoride-modified montmorillonite clay catalyst is employed in U.S. Pat. No. 5,157,161, to Texaco Chemical Co., to produce alkyl tertiary alkyl ethers.

In U.S. Pat. No. 5,183,947, to Texaco Chemical Co., fluorophosphoric acid-modified clays are employed as catalysts in a method to produce alkyl tertiary alkyl ethers.

In allowed U.S. Ser. No. 07/917,218, assigned to Texaco Chemical Co., there is disclosed the use of a super acid alumina or a faujasite-type zeolite to produce alkyl tertiary alkyl ethers.

Allowed U.S. Ser. No. 07/878,121, to Texaco Chemical Co., discloses the use of a haloacid-modified montmorillonite clay catalyst to convert $C_1$-$C_6$ primary alcohols and $C_4$-$C_{10}$ tertiary alcohols to alkyl tertiary alkyl ethers.

Fluorophosphoric acid-modified zeolites are employed in allowed U.S. Ser. No. 07/917,885, to Texaco Chemical Co., to produce alkyl tertiary alkyl ethers.

Sulfur promoted and "superacid" catalysts are known in the art. Superacid catalysts are particularly desirable for reactions where lower temperatures are favored. In an article titled "Design of Sulfur-Promoted Solid Superacid Catalyst" by K. Tanabe and T. Yamaguchi in "Successful Design of Catalysts," Inui, T. (Editor) Elsevier Science Publishers B. V., Amsterdam, 1988, p. 99, there is a discussion of the extremely high catalytic activities of sulfur-promoted superacids, including the factors controlling super acidity. Solid superacids such as $SO_4^{2-}/ZrO_2$, $SO_4^{2-}/TiO_2$ and $SO_4^{2-}/Fe_2O_3$ have been reported to exhibit extremely high catalytic activities for acylation and alkylation of aromatics, esterification of phthalic acid, skeletal isomerization of paraffins, dehydration of alcohols, polymerization of alkyl vinyl ethers, liquefaction of coal and rearrangement of oximes.

It is noted that the strength of the superacid depends on the extent of losing the S=O double bond character by an electronic shift from an adsorbed basic molecule to the sulfur complex. The larger the shift, the higher the acid strength.

The acid strength can vary depending on the preparation method, however, the acid strength of $SO_4^{2-}/ZRO_2$ is apparently 10,000 times higher than that of 100% $H_2SO_4$. The effect of the addition of $SO_4^{2-}$ on catalytic activity is surprisingly large.

Ibid., page 101, there is a comparison of the acidities achieved by introduction of various sulfur compounds, such as ammonium sulfate, $SO_3$, $SO_2$, or $H_2S$, onto $ZrO_2$, $TiO_2$, $Fe_2O_3$, $Al_2O_3$, $SnO_2$, $SiO_2$ and $Bi_2O_3$. From a comparison of experimentally obtained spectra of sulfur-promoted oxides under various conditions, it was observed that whatever the starting sulfur compounds are, once they were oxidized on the surface of $ZrO_2$, $TiO_2$ and $Fe_2O_3$, they form a structure in which the presence of two covalent SO double bonds is characteristic. The structure is responsible for the generation of the strong acidity and a central metal cation plays as a Lewis acid site. The formation is basically a chemical reaction between $SO_4^{2-}$, $SO_2$ or $SO_3$ and the oxide surfaces to form the definite structure in which two covalent bonds are involved.

Results indicated that when a basic molecule is adsorbed on the central metal cation, it tends to reduce the bond order of SO from a highly covalent double-bond character to a lesser double-bond character.

The stability of the catalyst upon hydrogen reduction at various temperatures, and the facility of regeneration upon reoxidation was tested using the dehydration of 2-propanol as the test reaction. The catalytic activity decreased with increase in reduction temperature from 100° to 450° C. It was theorized that the activity loss by reduction at lower temperatures might be the result of the removal of surface oxygens since recovery of the catalysts by oxidation was possible to varying extents.

It was observed that only $ZrO_2$, $TiO_2$ and $Fe_2O_3$ gave strong acidity by sulfur promotion, possibly because the number of acid-sites thus obtained may be limited by the surface area of the oxides.

In an article by O. Saur et al., J. Catal., 99, (1986) 104–110 titled "The Structure and Stability of Sulfated Alumina and Titania," sulfated alumina and titania were studied using infrared spectroscopy and a vacuum microbalance with the aim of determining the structure of the surface sulfate, its thermal stability, and its reducibility in $H_2$. It was concluded that the sulfated $TiO_2$ or $Al_2O_3$ has a structure resembling $(M_3O_3)S=O$ [M=Al or Ti], whereas in the presence of $H_2O$ or excess surface OH groups, this is converted to

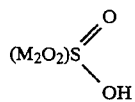

type groups, thus accounting for the increased Bronsted activity. Finally, the sulfated $Al_2O_3$ surface was found to be both more thermally stable and more resistant to reduction in $H_2$ than the sulfated $TiO_2$ and the authors state, "sulfates of titania are known to be relatively unstable."

In Catalysis Today, 5 (1989) 493–502 there is an article titled "n-Butane Isomerization on Solid Superacids," by J. C. Yori et al., in which the use of $ZrO_2/SO_4^{2-}$ to isomerize n-butane and method of preparation of $ZrO_2/SO_4^{2-}$ is discussed. The $ZrO_2/SO_4^{2-}$ was calcinated at between 773° K. and 933° K. and optimum catalytic activity was found where calcination took place around 893° K.

Ishida et al. report in Chem. Lett., 1869, 1988 on the "Acid Property of Sulfur-Promoted Zirconium Oxide on Silica as Solid Superacid." Here it was concluded that the higher acid strength of the catalyst can best be achieved after the crystal growth of the supported oxide, and that a tetragonal form of $ZrO_2$ grows extensively when the amount of $ZrO_2$ loaded becomes large. This relationship between crystal growth and generation of acidity may be of significance in designing a catalyst having a higher number of acid sites.

More recently, in an article titled "Recent Progress in Solid Superacid," in Applied Catalysis, 61 (1990) 1–25, T. Yamaguchi reviews literature on solid superacids including a discussion of mounted acids, combined acids, and sulfate-promoted metal oxides. It is noted at page 13 that sulfate-promoted metal oxides are useful as catalysts for skeletal isomerization of paraffins, polymerization of ethers, acetylation, benzolation and esterification.

Sulfate-containing solid superacids have been employed for acid-catalyzed hydrocarbon conversions by I. Rodriguez-Ramos et al., Division of Petroleum Chemistry, American Chemical Society, New York City Meeting, Aug. 25–30, 1990, preprints, p. 804. Here, a number of alumina and carbon carriers that had been impregnated with aqueous solutions of iron or zirconium nitrates, then reimpregnated with ammonium sulfate solutions, were tested in MTBE synthesis from methanol plus isobutene (Eq. 1). All catalysts were considerably less active than AMBERLYST ® A-15, a styrene-divinylbenzene polymer with sulfonic acid functionality. This difference in activity appears from the data to be a factor of about 40, even where the AMBERLYST ® A-15 was evaluated at a lower esterification temperature (70° C. versus 95°–120° C.).

There is a discussion titled "Dehydration of Alcohols Catalyzed by Metallic Sulphates Supported on Silica Gel," in J. Chem. Soc. Perkin Trans. I, 1989, 707, authored by T. Nishiguchi and C. Kamio. In this work metallic sulphates and hydrogen sulphates supported on silica gel efficiently catalyzed dehydration of secondary and tertiary alcohols under mild conditions. The dehydration catalytic activity of the sulphates and hydrogen sulphates was examined in the case of cyclododecanol. The sulphates of Ce, Ti and Fe were most active. Silica gel was essential for the efficient dehydration in each case.

The indication was that this type catalyst was unsuitable for primary alcohols. On page 709, Col. 1, lines 3–5, it is stated that primary alcohols failed to react.

The authors suggest that the greater the Lewis acidity of a sulphate, the greater its activity on silica gel and, further, that the proton liberated from hydrogen sulphates presumably contributes to the high activity of the salts because the salts of Na, K and $NH_4$ on silica gel were inactive.

Silica gel is quite distinct from other forms of silica. The following chart describes the properties of silica gels and indicates how they are different from other forms of silica:

TABLE 1
Properties of Different Forms of Amorphous Silica

| Property | Silica sols | Dry silica gels | Silica Precipitated from solution | Pyrogenic Silica |
|---|---|---|---|---|
| $SiO_2$, % | 10–15 | 96.5–99.6 | 80–90 | 99.7–99.9 |
| CaO, % | na | na | 0.1–4 | na |
| $Na_2O$, % | 0.1–0.8 | 0–1 | 0–1.5 | na |
| wt loss, % | | | | |
| at 105° C. | 50–80 | na | 5–7 | 0.5–2.5 |
| at 1200° C. | 50–90 | 2–17.5 | 10–14 | 0.5–2.5 |
| ultimate particle size, nm | 5–100 | 1–100 | 10–25 | 1–100 |
| aggregate particle size, μm | | 3–25 | 1–10 | 2–3 |
| surface area, $m^2/g$ | 50–700 | 200–700 | 45–700 | 15–400 |
| pH, aqueous suspension | 3–5, 8–11 | 2.3–7.4 | 4–9 | 3.5–8 |
| apparent or bulk density, $g/cm^3$ | 1.2–1.4 | 0.1–0.8 | 0.03–0.3 | 0.03–0.12 |
| true density, $g/cm^3$ | 2.2–2.3 | 2.22 | 2.0–2.1 | 2.16 |
| refractive index, $n_D$ | 1.35–1.45 | 1.35–1.45 | 1.45 | 1.45 |
| oil absorption, g/g | | 0.9–3.15 | 1–3 | 0.5–2.8 |

Silica gels are classified into three types, i.e., regular, intermediate and low-density. Regular density gel is made by gelling in an acid medium, which gives very small particles with high surface area. It generally contains about ca 6 wt % water as surface hydroxyl groups, which imparts a high capacity for water absorption and absorption of other polar molecules. It exhibits a high selectivity for polar molecules and contains a large percentage of small pores, see Kirk Othmer Encyclopedia of Chemical Technology, 3rd Ed., Vol. 20, p. 763.

Intermediate density silica gel has a lower surface area, but larger pore volume. It has a high capacity for water absorption at high humidities.

Low density silica gel has a lower surface area and large average pore diameter. It is usually prepared as a very fine powder of extremely low density.

It is known in the art to use silica gel as a desiccant, as an adsorbent, as a catalyst base, to increase viscosity and thixotropy, for surfactant and optical effects, as a source of reactive silica, for cloud seeding, in chromatographic column packing, as an anticaking agent, and in paper coating.

There is a desire in the art to identify catalysts which would be suitable for producing MTBE. It would be especially desirable to identify catalysts which allow the reaction to be accomplished in one step under relatively mild conditions and show good activity. Although some of the work discussed above suggests the isomerization of alkanes or dehydration of alcohols, there seems to be nothing in the art which would suggest reacting a primary and tertiary alcohol such as methanol and t-butanol over a heterogeneous catalyst where alkylsulfonic acid is bonded to an oxide to produce MTBE and isobutylene. It has now been discovered that a catalyst composition comprising alkylsulfonic acid on a Group III or IV metal oxide provides an active catalyst for MTBE synthesis.

SUMMARY OF THE INVENTION

In accordance with certain of its aspects, the novel method of this invention for preparing ethers from primary alcohols and tertiary alcohols, and especially methyl tert-butyl ether from tertiary butyl alcohol (t-butanol) and methanol in one-step, comprises reacting tertiary butyl alcohol and methanol in the presence of a heterogeneous catalyst comprising a silica gel having an alkylsulfonic acid moiety covalently bonded to it, whereby the composite acid has the following structure:

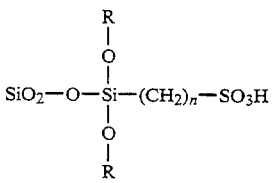

wherein R is an alkyl group having from 1 to 10 carbon atoms and n is an integer in the range of 1 to 100.

DESCRIPTION OF THE INVENTION

Preparation of the product of this invention may be carried out typically by the etherification in one step of tertiary alcohols with primary alcohols in the presence of a catalyst which preferably comprises an alkylsulfonic acid on a Group III or IV oxide.

The reaction can be represented by the following:

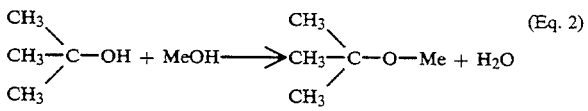

The reactants comprise mixtures of primary alcohols and tertiary alcohols which can be reacted over the catalyst to produce alkyl tertiary alkyl ethers. For example, methanol and t-butanol (tBA) coreactants are reacted to form MTBE and may be mixed in any proportion in order to generate the desired methyl t-butyl ether, but preferably the molar ratio of methanol to t-butanol in the feed mixture should be between 10:1 and 1:10, if the yield of desired MTBE is to be maximized. In order to achieve maximum selectivity to MTBE, and optimum conversion per pass, an excess of methanol in the liquid feed is desirable. The most preferred methanol-to-tertiary butanol molar ratio is from 1:1 to 5:1.

In certain circumstances, it may be particularly desirable that the t-butanol conversion be high enough (e.g. >40% per pass), such that the crude product mix phase separates into an isobutylene-MTBE product-rich phase and a heavier aqueous methanol phase. Preferably such a product phase separation would be achieved at as low an etherification temperature as possible, but particularly in the range 160°–200° C.

The same process may also be applied to the preparation of other alkyl tertiary alkyl ethers, such as, for example ethyl t-butyl ether (ETBE), TAME, etc. Said process may be applied to the reaction of a $C_1$–$C_6$ primary alcohol such as methanol, ethanol n-propanol and n-hexanol with a $C_4$–$C_{10}$ tertiary alcohol such as, for example, tertiary butanol and tertiary amyl alcohol. Reaction of methanol with tertiary amyl alcohol (2-methyl-2-butanol) would then yield methyl tertiary amyl ether (TAME). Alternatively a mixture of alcohols, e g., a mixture of $C_1$–$C_5$ alcohols, could be reacted to give a mixture of alkyl tert-alkyl ethers.

The alkylsulfonic acids bonded to the silica gel are considered derivatives of hydrocarbons in which a hydrogen atom has been replaced by the sulfonic acid group, (.$SO_2$.OH), having the general formula R.$SO_2$-

.OH. They are viscous liquids or crystalline solids which are soluble in water. Industrial applications of the alkylsulfonic acids are rather limited, although the corresponding aryl derivatives are decidedly important.

Examples of alkylsulfonic acids include methylsulfonic, ethylsulfonic, n-propylsulfonic, isopropylsulfonic and hexylsulfonic acids. Particularly good results were observed using n-propylsulfonic acid.

The catalysts used to effect this reaction are silica gel alkylsulfonic acids. As used in this application, the term "silica gel alkylsulfonic acids" means silica having alkylsulfonic acid groups chemically bound thereto. In other words, the alkylsulfonic acids are not merely deposited on the silica, but covalently bonded to the silica. Other catalysts within the scope of the present inventive process include alkylsulfonic acids bound to other Group IV oxides, such as titania, zirconia, and the like, or bound to Group III oxides, such as alumina, and the like.

Preferably, the silica gel alkylsulfonic acids used in the present invention have the following structure:

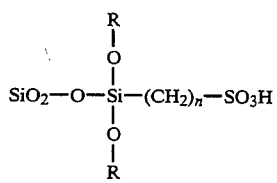

wherein R is an alkyl group having from 1 to 10 carbon atoms, preferably 1 to 3 carbon atoms and n is an integer in the range of 1 to 100, but preferably 3 to 10. More preferably, the silica gel alkylsulfonic acid used in the present invention is silica gel propylsulfonic acid. The preparation of silica-bound sulfonic acids is exemplified herein by the preparation of silica gel propylsulfonic acid.

The oxide support may be in the form of powders, pellets, spheres, shapes and extrudates. For some applications, the silica gel is converted to pelletized or granular form by extruding pulverized gel with a binder, or shaping during drying. Freezing of a silica gel produces silica-gel particles of nonspherical shapes.

Silica gels can be prepared by the bulk-set process, the slurry process and hydrolysis of pure silicon compounds.

Once a gel structure is formed, it can be modified in the wet state to strengthen the structure or enlarge pore size and reduce surface area. This is discussed in Kirk Othmer, supra, pg. 775. The examples described herein demonstrate the advantages of using granules. Silica gel can be prepared by extrusion or by compaction in conventional pelleting apparatus using a pelleting aid such as graphite.

As will be demonstrated by the examples, the silica gel supports are preferably of high purity and $>10$ m$^2$/g surface area, most preferably $>100$ m$^2$/g. It has been found in the process of this invention that greater conversion of tertiary butanol and methanol is achieved where the surface area of the support is generally $>10$ m$^2$/g.

The weight percent of alkylsulfonic acid to oxide support should be such that the concentration of the sulfur in the formulated catalyst is in the range of 0.1 wt % to 30 wt %, although concentrations outside this range may also be employed. Where propylsulfonic acid, for example, is bonded to silica gel, a suitable quantity of sulfur is $>0.1$ wt %.

Silica gels are commercially available in at least the following mesh sizes 3–8, 6–16; 14–20; 14–42; and 28–200 and greater. A suitable commercially available silica gel is the grade 12, 28–200 mesh, silica gel available from Aldrich Chemical Co., Inc. having a surface area of 800 m$^2$/g. Silica gel propylsulfonic acid may be prepared by treating silica gel with (3-mercaptopropyl)-trimethoxysilane. The resulting surface-modified mercaptan is then oxidized using aqueous H$_2$O$_2$, to give the silica-bound sulfonic acid.

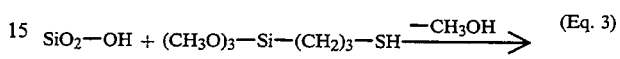

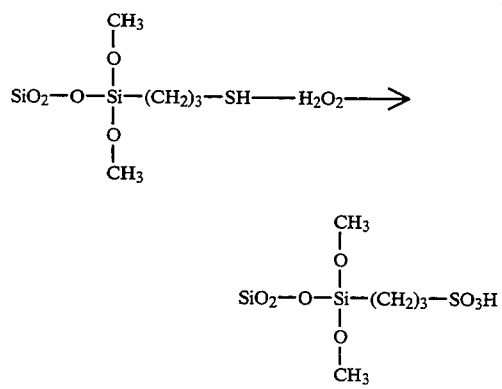

This and other procedures are more fully described by R. D. Bradley and W. T. Ford, in "Silica-Bound Sulfonic Acid Catalysts," J. Org. Chem., Vol 54, No. 23, pp 5437–5443 (1989), incorporated herein by reference, and in Example I of this application.

The silica gel alkylsulfonic acid composition of the present invention is preferably employed as a fixed bed of catalyst in a continuous reaction system. In a continuous process of this nature, the time of contact of the reactants with the catalyst is one of the interrelated factors that those skilled in the art will adjust, along with temperature, pressure, bed geometry, pellet size, etc. in order to obtain a desired rate of reaction and, hence, a desired percentage of conversion of the reactants. Thus, in a continuous process, it is not necessary to drive the reaction to completion because unreacted feedstock components can be recycled to the reactor.

Catalyst life is an important factor in conducting a continuous reaction. For example, if a catalyst is easily poisoned, or if catalyst pellets do not have good structural properties, the economics of the process will be adversely affected. The catalysts of the present invention are relatively insensitive to poisoning, so this should not present a problem.

As a consequence, the catalyst compositions of the present invention are advantageously used in a continuous process for the continuous production of methyl t-butyl ether reaction products from tertiary butanol and methanol. Such catalyst compositions should be suitable for use for prolonged periods without the need for regeneration. Nevertheless, with the passage of time deactivation will tend to slowly occur. Deactivation can be measured qualitatively by the loss of butanol conversion, or as the increase of temperature required to maintain an essentially constant conversion rate for the t-butanol and methanol.

The fact that this method can be achieved under relatively mild operating conditions is an attractive feature of this invention. Etherification can generally be conducted at temperatures from 20° to 250° C. The preferred range is 100° to 200° C. The total operating pressure may be from 0 to 1000 psig, or higher. The preferred pressure range is 50 to 500 psig.

Typically, MTBE is generated continuously in up to ca. 40 wt % concentration in the crude liquid product at total liquid hourly space velocities (LHSV) of at least 0.1 and up to ten, and relatively mild conditions, where:

$$LHSV = \frac{\text{Volume Of Total Liquid Feed Run Through The Reactor Per Hour}}{\text{Volume of Catalyst In Reactor}}$$

The examples which follow illustrate the one-step synthesis of MTBE from tBA and MeOH (Eq. 2) using propylsulfonic acid-modified silica gel. The examples are only intended as a means of illustration and it is understood the invention is not meant to be limited thereby.

Conversion of t-butanol (tBA, wt %) is estimated in the 15 following examples using the equation:

$$\frac{(\text{Wt \% Conc. of } tBA \text{ in Feed} - \text{Wt \% Conc. of } tBA \text{ in Product})}{\text{Wt \% Conc of } tBA \text{ in Feed}} \times 100$$

Selectivities to methyl t-butyl ether (MTBE, mole %) are estimated from:

$$\frac{\text{Moles of } MTBE \text{ in Product Liquid}}{\text{Moles of } tBA \text{ Converted}} \times 100$$

Comparing the MTBE/isobutylene production in Table 1 and Example 2 using the propylsulfonic acid-modified silica gel catalyst prepared by the method of Example 1, with data for the untreated silica gel of Example 3 and Table II, it may be noted that:

a) Only the propylsulfonic acid-treated silica gel gave significant quantities of the desired MTBE/isobutylene products.
b) Only the propylsulfonic acid-treated silica gel achieves product phase separation into an isobutylene-MTBE product-rich phase and a heavier aqueous methanol place at the 160°–180° C. operating temperatures Only the propylsulfonic acid-treated silica gel gives near equilibrium tBA conversion levels over the full operating temperature range (120°–180° C.) when using a 1.1:1 MeOH/tBA feed mix.

The examples which follow illustrate the one-step method of this invention. The examples are only intended as a means of illustration and it is understood the invention is not meant to be limited thereby.

EXAMPLE 1

This example illustrates the preparation of a propylsulfonic acid-modified silica gel.

To 500 g of silica gel (Grade 12, 28–200 mesh, 800 m²/g surface area) was added 1000 g of 10% hydrochloric acid solution and the mixture heated to reflux for 4 hours. The product solids were washed with distilled water until the washings were pH neutral and then dried in vacuo at 100° C. About 500 g of the acid-treated silica gel was next refluxed with toluene (1000 g) for 5 hours, 125 g of (3-mercaptopropyl)trimethoxysilane added and the new mix refluxed for an additional 25–30 hours. Solids from the crude product were recovered by filtration, washed with acetone and toluene and dried in vacuo at 100° C.

The mercapto silica gel from above was then added to an aqueous solution of hydrogen peroxide (30%, 1500 g) in distilled water (400 g) and the mixture stirred slowly at ambient temperature, overnight. The red-brown product granules were recovered by filtration, washed with water, acetone and toluene, then dried in vacuo at 100° C., overnight. Analyses were as follows:
$H_2O$: 0.54%
Acidity: 0.48 meq/g
Sulfur: 1.7%

EXAMPLE 2

This example illustrates the production of methyl t-butyl ether from t-butanol and methanol using a propylsulfonic acid-modified silica gel catalyst.

Synthesis was conducted in a tubular reactor (⅜" id, 12" long) constructed of 316 stainless steel, operated upflow and mounted to a furnace controllable to ±10° C. and fitted with pumps allowing flow control to ±1 cc/hr. The reactor was also fitted with a pressure regulating device and equipment for monitoring temperature, pressure and flow rate.

The reactor was charged at the beginning of the experiment with 25 cc of propylsulfonic acid-modified silica gel granules, prepared by the method of Example 1. A screen of glass wool was placed at the top and bottom of the reactor to ensure the catalyst would remain in the middle portion.

The catalyst bed was treated with a methanol/t-butanol (1.1:1 molar mix), upflow, at a rate of 50 cc/hr, while the reactor held at a series of operating temperatures (120°–180° C.). Pressure was maintained at 300 psi. Samples of crude product effluent were collected on stream at each temperature and analyzed by glc and gc-ir. Sample analyses data are given in Table I. Calculated tBA conversions and $C_4H_8$/MTBE selectivities for typical samples are as follows:

| Sample | Operating Temp (°C.) | tBA Conv. (%) | Molar Selectivity (%) | |
|---|---|---|---|---|
| | | | $C_4H_8$ | MTBE |
| 2 | 120 | 67 | 21 | 74 |
| 3 | 140 | 71 | 34 | 67 |
| 6 | 160 | 91 | a | a |

[a]Not determined

TABLE I

MTBE/ISOBUTYLENE SYNTHESIS

| Ex. | Catalyst | MeOH/tBA Molar Ratio | Feed Rate (cc/hr) | Temp. (°C.) | Time On Stream (Days) | SAMPLE | H$_2$O | MeOH | C$_4$H$_8$ | tBA | MTBE |
|---|---|---|---|---|---|---|---|---|---|---|---|
| 2 | Ex. 1 | 1.1:1 | 50 |     |   | FS-1 |      | 30.9 |      | 69.0 |      |
|   |       |       |    | 120 | 1 | 1    | 11.6 | 17.7 | 7.0  | 23.2 | 40.2 |
|   |       |       |    |     |   | 2    | 11.6 | 17.5 | 7.4  | 22.8 | 40.5 |
|   |       |       |    | 140 | 2 | 3    | 11.8 | 18.1 | 12.6 | 19.9 | 36.9 |
|   |       |       |    |     |   | 4    | 12.1 | 18.4 | 12.5 | 20.3 | 36.0 |
|   |       |       |    | 160 | 3 | 5    | 2.2  | 11.6 | 53.6 | 5.8  | 26.4 |
|   |       |       |    |     |   |      | 38.4 | 44.1 | 3.6  | 7.1  | 6.6  |
|   |       |       |    |     |   | 6    | 2.1  | 11.3 | 54.0 | 5.7  | 26.7 |
|   |       |       |    |     |   |      | 38.2 | 44.5 | 3.5  | 7.1  | 6.5  |
|   |       |       |    | 180 | 4 | 7    | 3.9  | 13.9 | 65.8 | 3.3  | 12.4 |
|   |       |       |    |     |   |      | 40.8 | 48.1 | 2.7  | 5.6  | 2.6  |
|   |       |       |    |     |   | 8    | 1.2  | 10.8 | 71.0 | 3.3  | 13.1 |
|   |       |       |    |     |   |      | 39.7 | 48.6 | 2.9  | 5.9  | 2.6  |

EXAMPLE 3

This comparative example illustrates the performance of an unmodified silica gel in the production of methyl t-butyl ether from t-butanol and methanol over a range of conditions.

Using the equipment and procedures of Example 2, 25 cc of silica gel granules (Aldrich Chemical, Grade 12, 28–200 mesh) was charged to the reactor system and performance was monitored over a range of operating temperatures (120°–180° C.). The results are summarized in Table II, only trace quantities of isobutylene/MTBE products were detected.

TABLE II

MTBE/ISOBUTYLENE SYNTHESIS

| Ex. | Catalyst | MeOH/tBA Molar Ratio | Feed Rate (cc/hr) | Temp. (°C.) | Time On Stream (Days) | SAMPLE | H$_2$O | MeOH | C$_4$H$_8$ | tBA | MTBE |
|---|---|---|---|---|---|---|---|---|---|---|---|
| 3 | SiO$_2$[a] | 1.1:1 | 50 |     |   | FS-1 |     | 31.2 |     | 68.6 |     |
|   |           |       |    | 120 | 1 | 1    | 0.9 | 30.2 | 0.5 | 66.5 | 1.7 |
|   |           |       |    |     |   | 2    | 0.7 | 30.2 | 0.4 | 67.3 | 1.2 |
|   |           |       |    | 140 | 2 | 3    |     | 30.9 | 0.1 | 68.8 |     |
|   |           |       |    |     |   | 4    |     | 30.9 | 0.1 | 68.7 |     |
|   |           |       |    | 160 | 3 | 5    |     | 30.8 | 0.1 | 68.7 |     |
|   |           |       |    |     |   | 6    | 0.2 | 30.7 | 0.2 | 68.7 |     |
|   |           |       |    |     |   | 7    | 0.1 | 31.3 | 0.1 | 68.2 |     |
|   |           |       |    | 180 | 4 | 8    | 0.1 | 31.1 | 0.1 | 68.5 |     |

[a]Aldrich, Grade 12, 28–200 Mesh

What is claimed is:

1. In a method for the synthesis of methyl t-butyl ether from t-butanol and methanol in one step, the improvement comprising accomplishing the reaction in one step, using a heterogeneous catalyst comprising an alkylsulfonic acid covalently bonded to an oxide of Group III or IV of the Periodic Table.

2. The method of claim 1, wherein the Group III or IV oxide is selected from the group consisting of zirconia, titania, silica and alumina.

3. The method of claim 1 wherein the oxide is silica gel.

4. The method of claim 1 wherein the alkylsulfonic acid is selected from the group consisting of methylsulfonic, ethylsulfonic, n-propylsulfonic and isopropylsulfonic.

5. The method of claim 4 wherein the alkylsulfonic acid is propylsulfonic acid.

6. The method of claim 5 wherein the oxide is silica gel on the operating temperature is in the range of 160° to 180° C. and the product comprises a two-phase mix of an isobutylene-MTBE product rich phase and a heavier aqueous methanol-rich phase.

7. The method of claim 1 wherein the oxide is silica gel and the silica alkylsulfonic acid moiety has the following structure:

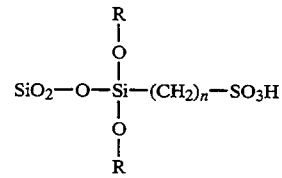

wherein R is an alkyl group having from 1 to 10 carbon atoms and n is an integer in the range of 1 to 100.

8. The method of claim 1 wherein the temperature is from about 100° C. to 200° C.

9. In a method wherein t-butanol is reacted with methanol to provide methyl t-butyl ether, the improvement comprising accomplishing the reaction in one step using a catalyst consisting essentially of silica gel having an alkylsulfonic acid covalently bonded thereto, contacting said t-butanol and methanol in a molar amount of 0.1 to 10 moles of methanol per mole of t-butanol at a temperature of 20° C. to 250° C. and a pressure of about atmospheric to about 1000 psig and obtaining the MTBE product, where the silica alkylsulfonic acid moiety has the structure:
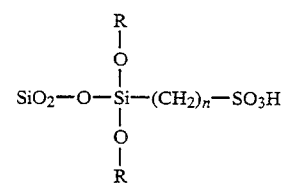
for which R is an alkyl group having from 1 to 3 carbon atoms and n is an integer in the range of 3 to 10.
* * * * *

UNITED STATES PATENT AND TRADEMARK OFFICE
CERTIFICATE OF CORRECTION

PATENT NO. : 5,338,890
DATED : August 16, 1994
INVENTOR(S) : John F. Knifton
John R. Sanderson It is certified that error appears in the above-indentified patent and that said Letters Patent is hereby corrected as shown below:

Column 12, claim 6, line 26, second word,
delete "on" and insert --and--.

Signed and Sealed this

Eighteenth Day of October, 1994

Attest:

BRUCE LEHMAN

*Attesting Officer*         *Commissioner of Patents and Trademarks*